United States Patent
Nozaki et al.

[11] Patent Number: 6,129,719
[45] Date of Patent: Oct. 10, 2000

[54] URINE ABSORBENT PAD FOLDED INTO PROTECTIVE POSITION AFTER BEING SECURED TO WEARER'S PENIS

[75] Inventors: Satoshi Nozaki; Takashi Maeno, both of Ehime-ken; Makoto Utsunomiya, Chiba-ken; Yutaka Sakamoto, Kanagawa-ken, all of Japan

[73] Assignee: Uni-Charm Corporation, Ehime-ken, Japan

[21] Appl. No.: 09/027,924

[22] Filed: Feb. 23, 1998

[30] Foreign Application Priority Data

Feb. 28, 1997 [JP] Japan .................................. 9-046015

[51] Int. Cl.⁷ .............................. A61F 13/15; A61F 13/20
[52] U.S. Cl. ........................... 604/385.01; 604/385.01 M
[58] Field of Search .................................. 604/347, 349, 604/385.1, 386, 389, 395, 385.01, 385.09, 385.19

[56] References Cited

U.S. PATENT DOCUMENTS

| | | | |
|---|---|---|---|
| H1602 | 10/1996 | Brock ....................................... | 604/389 |
| 4,197,849 | 4/1980 | Bostick . | |
| 4,710,188 | 12/1987 | Runeman ............................. | 604/385.1 |
| 4,886,509 | 12/1989 | Mattsson ................................. | 604/349 |
| 5,074,853 | 12/1991 | Bryant ..................................... | 604/349 |
| 5,554,149 | 9/1996 | O'Donnell ............................... | 604/349 |
| 5,735,837 | 4/1998 | Ishikawa .................................. | 604/349 |
| 5,827,250 | 10/1998 | Fujioka et al. .......................... | 604/349 |

FOREIGN PATENT DOCUMENTS

| | | | |
|---|---|---|---|
| 296 08 682 U | 8/1996 | Germany . | |
| 61-60653 | 9/1986 | Japan . | |
| 2-6024 | 1/1990 | Japan . | |
| 406181942 | 7/1994 | Japan .................................... | 604/347 |
| 2 142 243 | 1/1985 | United Kingdom .................. | 604/349 |
| 2280374 | 2/1995 | United Kingdom . | |

OTHER PUBLICATIONS

Patent Abstracts of Japan No. 09 038126, Feb. 10, 1997.
Patent Abstracts of Japan No. 09 038127, Feb. 10, 1997.

*Primary Examiner*—Mark O. Polutta
*Attorney, Agent, or Firm*—Lowe Hauptman Gopstein Gilman & Berner

[57] ABSTRACT

A urine absorbent pad is folded along a transverse center folding line extending across a full length of the absorbent pad into upper and lower halves. An inner side of the absorbent pad is formed with adhesive zones extending over a desired extent of the respective side edges and one of the upper and lower halves divided by the transverse center folding line is formed with a guide arrangement for insertion of a wearer's penis extending through a thickness of the absorbent pad.

15 Claims, 5 Drawing Sheets

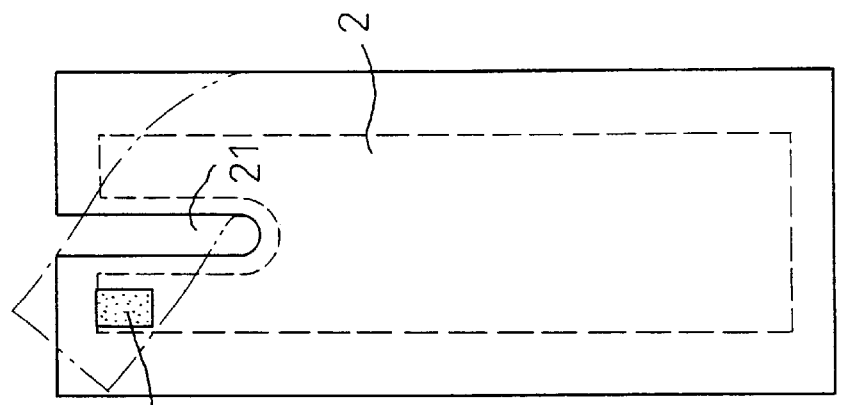
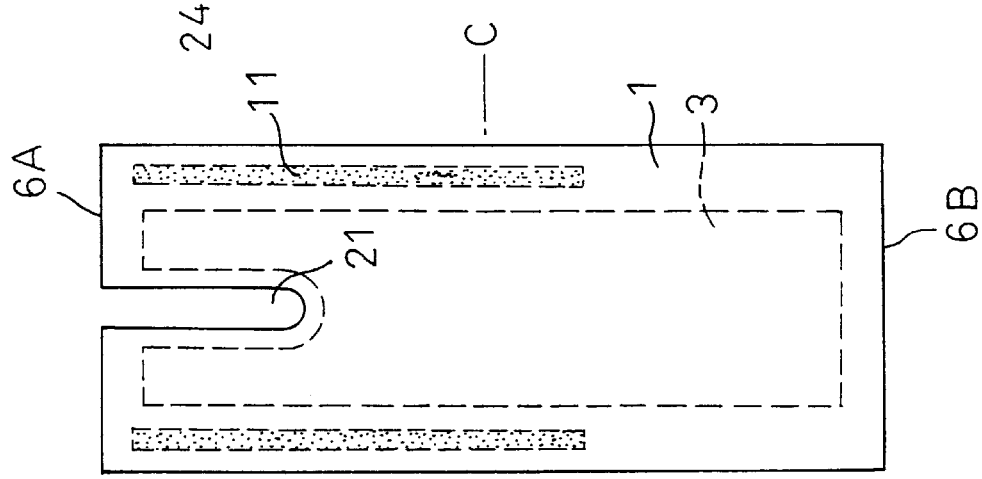
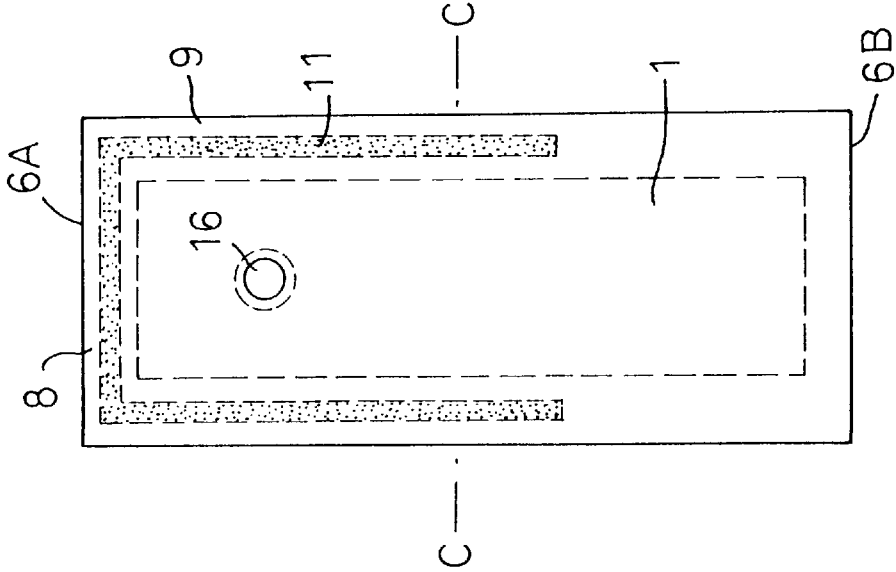

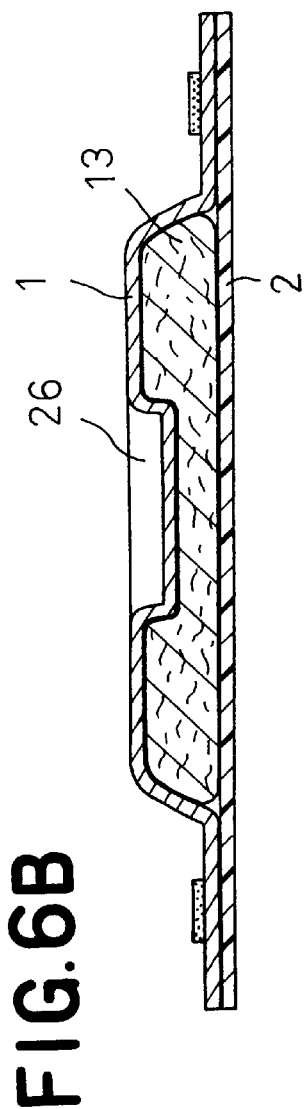
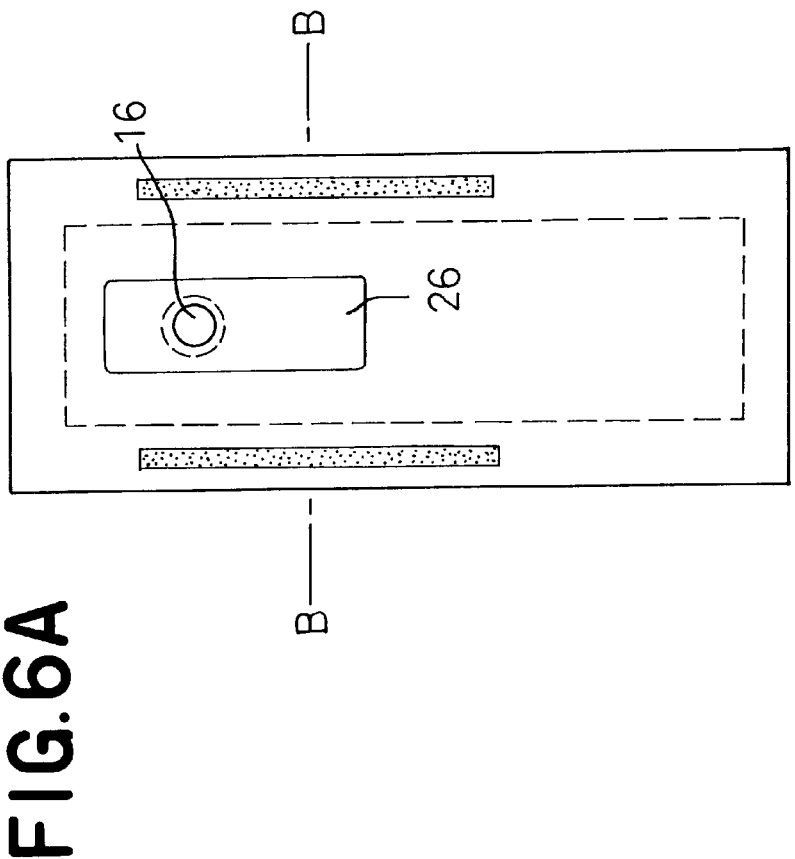
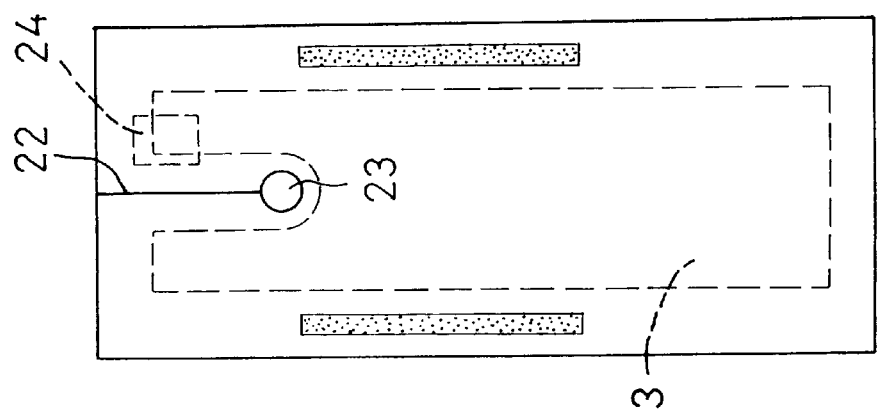

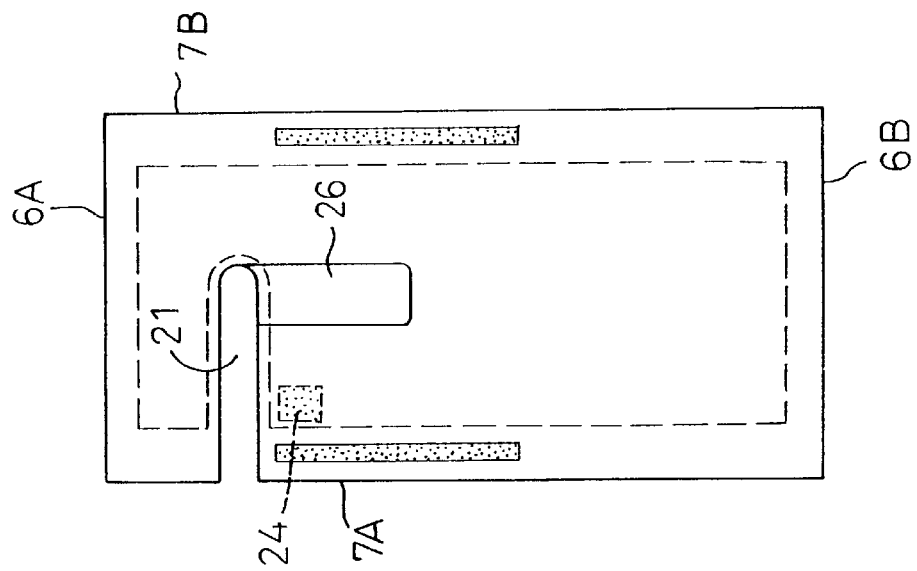
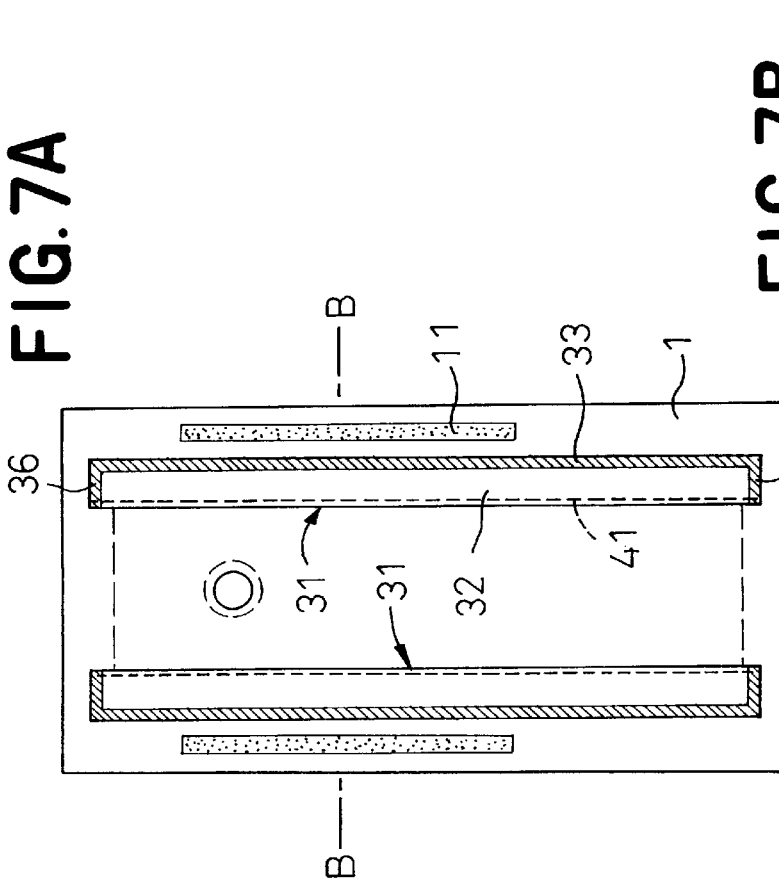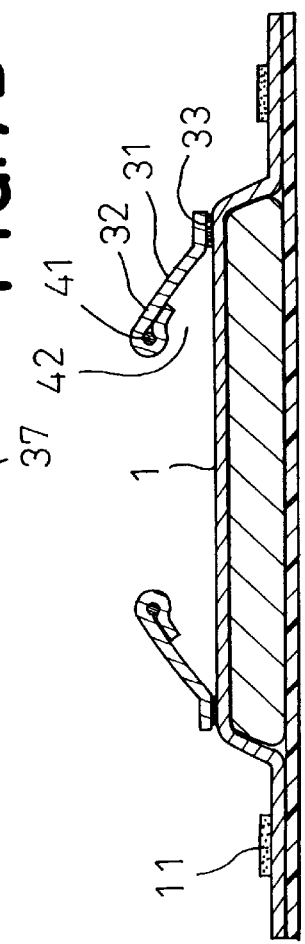

URINE ABSORBENT PAD FOLDED INTO PROTECTIVE POSITION AFTER BEING SECURED TO WEARER'S PENIS

TECHNICAL FIELD

This invention relates to urine absorbent pads for bedridden or incontinent men.

BACKGROUND OF THE INVENTION

A urination bag as disclosed in Japanese Utility Model Application Publication (Kokoku) No. Sho61-30653 is constructed so that a front side of a bag sealed along its periphery is tucked together with one of two absorbent layers contained within the bag along a cut line formed in the front side substantially in an inverted U-shape into the bag and thereby an opening for urination is obtained.

Japanese Utility Model Application Laid-Open (Kokai) No. Hei2-6024 discloses an absorbent pad in the form of a rectangular sheet having a strip of adhesive tape provided on a backsheet so that the rectangular sheet may be curved in the form of a hopper.

It is apparent from the description in the foregoing publication that the wearer's penis is inserted through the opening into the bag when the bag is worn, although no specific description can be found in the foregoing publication concerning such manner of use. However, it is rarely possible for the wearer to insert the penis by himself. It is difficult particularly for the elderly patient not only to insert the penis but also to wear such urination bag. Even if handling is possible for such a patient, it often takes much time and effort.

The foregoing sheet-like absorbent pad is curved in the form of a hopper and overlapping portions of the sheet are fastened together by means of the adhesive tape strip. This pad is effective for a relatively small quantity of urination but an increase in the quantity of urination may possibly cause a leakage of urine from the lower end of the hopper.

SUMMARY OF THE INVENTION

In view of the problem as described above, it is a principal object of the invention to provide a urine absorbent pad improved to be easily worn and substantially free from leakage of urine.

The object set forth above is achieved, according to the invention, by a urine absorbent pad comprising a liquid-permeable topsheet, a liquid-impermeable backsheet and a liquid-absorbent core disposed therebetween. Longitudinally opposite ends of the absorbent pad extend substantially parallel to each other transversely of the absorbent pad and transversely opposite side edges of the absorbent pad extending substantially parallel to each other longitudinally of the absorbent pad.

The absorbent pad is adapted to be folded with the topsheet lying inside along a folding line extending across a full width of the absorbent pad at a desired level, dividing the absorbent pad in longitudinally upper and lower halves. The absorbent pad is formed on an inner surface thereof with transversely opposite adhesive zones, each extending over a longitudinally given extent of each of the side edges including the folding line. One of the upper and lower halves divided by the folding line is formed with a guide arrangement extending through the absorbent pad from an inner surface to an outer surface thereof for insertion of a wearer's penis.

Preferably, the guide arrangement includes a circular through-hole, or a substantially U-shaped cutout extending from a middle of one end toward the other end of the absorbent pad so as to divide a portion of the absorbent pad in transversely two halves or a cutout substantially of U-shape extending from one of the side edges of the absorbent pad toward the other side edge and terminating at the transversely middle region so as to divide a portion of the absorbent pad limited by the cutout in upper and lower regions.

Preferably, a pair of flaps provided with elastic members are fixed to the inner surface of the absorbent pad along its transversely opposite side edges so that these flaps tend to stand erect on the inner surface of the absorbent pad as the pad is folded in two.

Preferably, the inner side of the absorbent pad is formed in a transversely middle region with a groove extending longitudinally of the absorbent pad.

BRIEF DESCRIPTION OF THE DRAWINGS

FIG. 3 is a plan view of another embodiment of the urine absorbent pad according to the invention;

FIG. 4 is an illustration of still another embodiment of the urine absorbent pad according to the invention in plan views as viewed from its inner side (A) and from its outer side (B);

FIG. 5 is a plan view of yet another embodiment of the urine absorbent pad according to the invention;

FIG. 6 shows a variant of the urine absorbent pad according to the invention in a plan view (A) and in a sectional view (B) taken along a line B—B;

FIG. 7 shows another variant of the urine absorbent pad according to the invention in a plan view (A) and in a sectional view taken along a line B—B; and FIG. 8 is a plan view showing still another variant of the urine absorbent pad according to the invention.

DESCRIPTION OF THE PREFERRED EMBODIMENT

Details of a urine absorbent pad according to the invention will be more fully understood from the description given hereunder in reference with the accompanying drawings.

Figure 1:
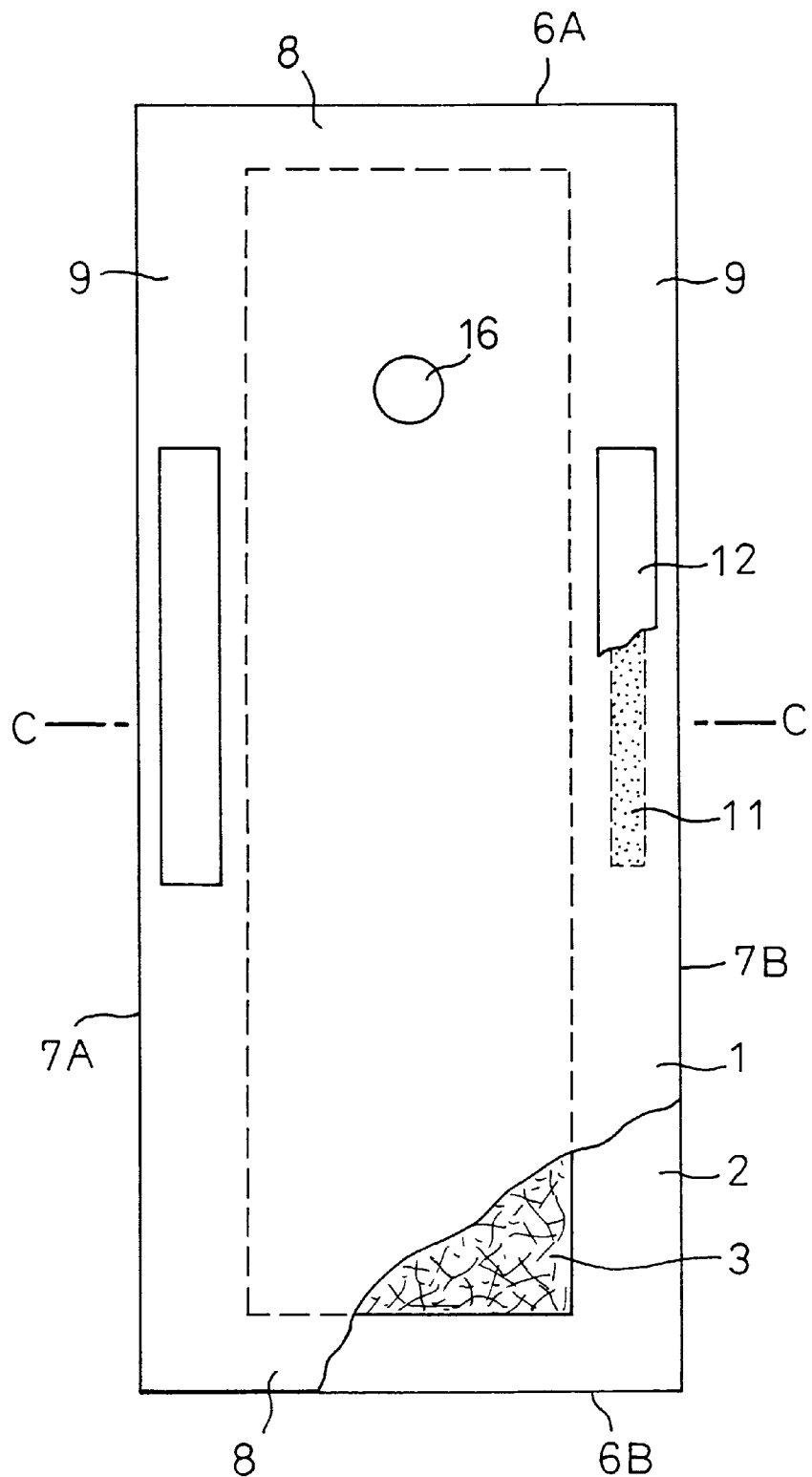
FIG. 1 is a plan view of an embodiment of a urine absorbent pad according to the invention as partially broken away.

A urine absorbent pad shown by FIG. 1 in a plan view as partially broken away comprises a liquid-permeable topsheet 1, a liquid-impermeable backsheet 2 and a liquid-absorbent core 3 disposed between these two sheets. The absorbent pad has a rectangular shape defined by longitudinally opposite ends 6A, 6B extending parallel to each other transversely of the absorbent pad and transversely opposite side edges 7A, 7B extending parallel to each other longitudinally of the absorbent pad. The topsheet 1 and the backsheet 2 are placed one upon another and bonded by means of hot melt adhesive or heat-sealed together along their portions extending outward beyond a peripheral edge of the absorbent core 3 to form end flaps 8 and side flaps 9.

In actual use, the absorbent pad is folded in two, for example, along a center line C—C dividing an effective region of the absorbent pad into two longitudinal halves with the topsheet 1 lying inside, as will be described later in more detail. Adhesive zones 11 are formed on an upper surface of the topsheet 1 on the respective side flaps 9 and extend upward longitudinally of the absorbent pad across the center line C—C over a relatively large extent so that the two halves of the folded absorbent pad may be reliably secured together along the adhesive zones 11. It should be understood that, as will be apparent from FIG. 1, the adhesive zones 11 are protectively covered with release paper sheets 12 before the absorbent pad is actually used. The upper half of the absorbent pad folded along the center line C—C is formed in its transversely middle location with a through-hole 16 for insertion of a wearer's penis.

Figure 2:
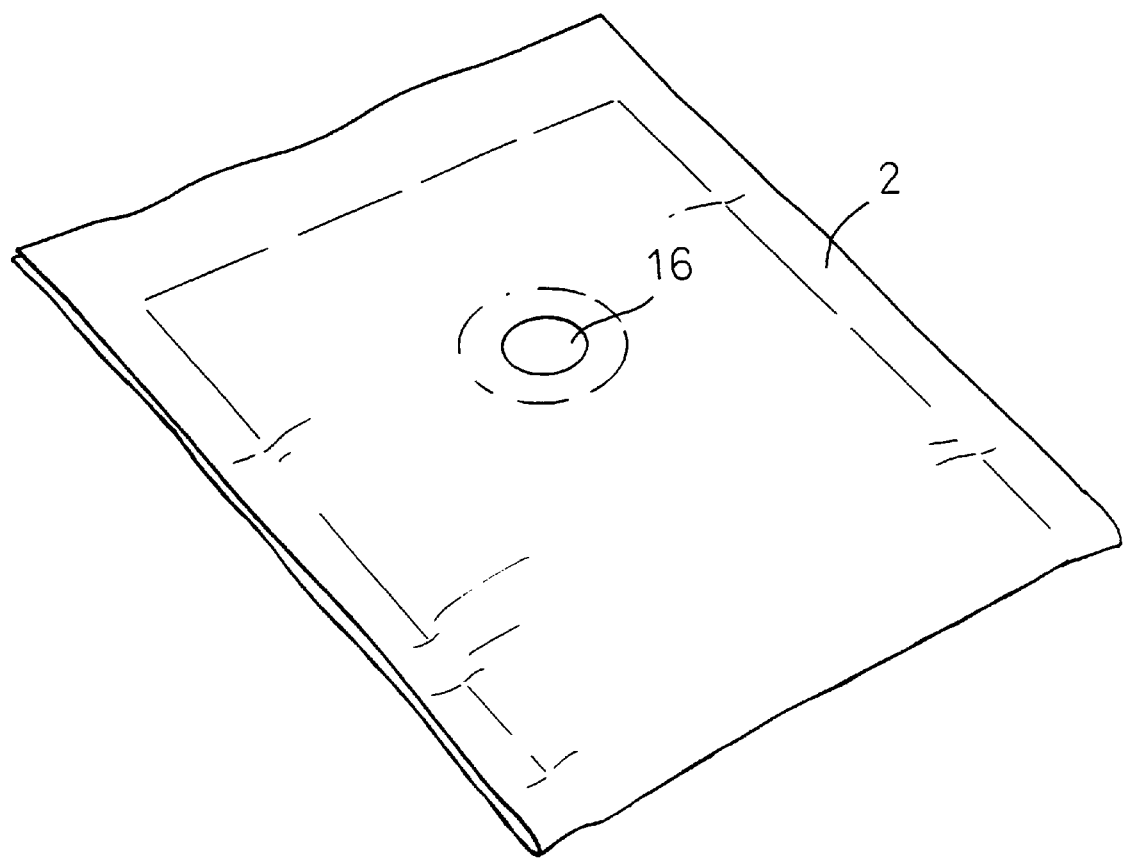
FIG. 2 is a perspective view of the urine absorbent pad as folded in two.

FIG. 2 is a perspective view of the absorbent pad as folded along the center line C—C, showing two halves of the folded absorbent pad placed one upon another and secured together along the adhesive zones 11. In actual use of the absorbent pad, the wearer's penis is inserted from the outer side of the backsheet 2, the release paper sheets 12 are then peeled off from the respective adhesive zones 11 and the absorbent pad is folded as shown by FIG. 2. The absorbent pad is removed from the wearer's penis after urination.

After the wearer's penis has been inserted into the through-hole 16, the absorbent pad is folded in two to form a bag wrapping the wearer's penis. To insert the wearer's penis into the through-hole 16, the wearer's finger tips may be inserted into the through-hole 16 from the side of topsheet 1 until the wearer's finger tips are exposed outside the backsheet 2 and the wearer's penis may be introduced into the bag-like absorbent pad. In this way, the wearer's penis can be reliably received in the bag-like absorbent pad to its proximal end. Consequently, the absorbent pad can be easily worn and, once having been put on the wearer's penis, there is no apprehension that the absorbent pad might easily fall off from the wearer's penis.

FIG. 3 is a view similar to FIG. 1 of another embodiment of the urine absorbent pad. With this embodiment of the absorbent pad, there is provided an adhesive zone 11 extending continuously along portions of the respective side flaps 9 and the upper end flap 8.

It is essential for this adhesive zone 11 to extend longitudinally of the absorbent pad at least from the center line C—C to the approximate level of the through-hole 16. However, it should be understood that the adhesive zone 11 may extend along a full length of each side flap 9 or extend further so as to cover the upper end flap 8 as shown by FIG. 3. When the absorbent pad illustrated by FIG. 3 is folded in two, a bag closed along its all sides is obtained.

FIG. 4 shows still another embodiment of the urine absorbent pad in views similar FIG. 1, in which FIG. 4(A) shows an inner side and FIG. 4(B) shows an outer side of the absorbent pad. With this absorbent pad, the circular through-hole 16 for insertion of the wearer's penis is replaced by a U-shaped cutout 21 extending from the middle of the upper end 6A toward the lower end 6B so as to divide an upper region of the absorbent pad transversely in two. The adhesive zones 11 extend along transversely opposite side edges from a level in the proximity of the center line C—C upward to a level adjacent the upper end 6A. The backsheet 2 of the absorbent pad is formed in the proximity of the cutout 21 with a fastening zone 24 so that transversely opposite sides of the absorbent pad defining the cutout 21 may be connected to each other as indicated by imaginary lines after the wearer's penis has been inserted into the cutout 21.

FIG. 5 is a view similar to FIG. 4 showing further another embodiment of the urine absorbent pad. With this absorbent pad, the guide means for insertion of the wearer's penis comprises a cut line (slit) 22 extending downward from the upper end 6A to divide an upper portion of the absorbent pad transversely in two and a circular through-hole 23 formed at the distal end of the cut line 22. With this absorbent pad, it is also possible to define the guide arrangement for insertion of the wearer's penis by the cut line 22 alone, if the circular through-hole 23 is considered to be unnecessary. The backsheet 2 is formed with the fastening zone 24 as in the case of the absorbent pad shown by FIG. 4.

FIG. 6 shows a variant of the invention in a plan view (A) and in a sectional view (B) taken along a line B—B in FIG. 6(A), respectively. This absorbent pad is formed in a transversely middle region with a groove 26 extending longitudinally of the absorbent pad. The groove 26 is defined by the topsheet 1 recessed toward the backsheet 2, i.e., a portion of the absorbent core 13 corresponding to this groove 26 is thinner than the rest of the absorbent core 13 as clearly depicted in FIG. 6B. The bottom of this groove 26 is formed with the through-hole 16 into which the wearer's penis is inserted and then laid within the groove 26 so that discharged urine may be absorbed by the absorbent pad substantially at the central zone thereof. The absorbent pad enables the wearer's penis to be controllably positioned within the groove 26 and thereby enables discharged urine to spread evenly along both sides of the groove 26. With the conventional absorbent pad which is not adapted to control the position of the inserted penis and tends to put the penis on one side of the absorbent core, only the region of the absorbent core limited in the proximity of the penis is rapidly saturated with the discharged quantity of urine. However the quantity of urine having been absorbed by this limited region of the absorbent core can not easily spread to the region of the absorbent core which is remote from the penis. As a result, the absorbent pad will be discarded without adequate use of a urine absorptivity of the absorbent core.

FIG. 7 shows another variant of the invention in which FIG. 7(A) is a view similar to FIG. 2 and FIG. 7(B) is a sectional view taken along a line B—B in FIG. 7(A). With this variant of the absorbent pad, inside the transversely opposite adhesive zones 11 there are provided a pair of flaps 31 opposed to each other. Each of flaps 31 extends longitudinally of the absorbent pad and is defined by transversely opposite side edges 32, 33 and longitudinally opposite ends 36, 37. The flap 31 is bonded to the topsheet 1 by means of hot melt adhesive (not shown) along its outer side edge 32 and longitudinally opposite ends 36, 37 as indicated by oblique lines. An elastic member 41 is attached under appropriate tension to the flap 31 along its inner side edge 32. Referring to FIG. 7(B), contraction of the elastic member 41 raises the flap 31 on the topsheet 1 with the outer side edge 33 remaining on the topsheet 1 as a proximal end and the inner side edge 32 lifting off from the topsheet 1 to form a pocket 42 opened inwardly of the absorbent pad. Such contraction of the elastic member 41 as well as raising of the inner side edge 32 occurs as the absorbent pad is folded in two as shown by FIG. 3. When the absorbent pad is in its unfolded state as shown by FIG. 7(A), the inner side edge 32 remains collapsed upon the topsheet 1 and the pocket 42 remains substantially closed. With the absorbent pad constructed as has been described above, the quantity of urine discharged and transversely flowing on the topsheet 1 is held by the pocket 42 and effectively prevented from leaking away from the absorbent pad.

FIG. 8 is a view similar to FIG. 2 showing further another variant of the invention. According to this variant, the U-shaped cutout 21 for insertion of the wearer's penis extends from the one side edge 7A toward the other side edge 7A and terminates in the proximity of the transversely middle region of the absorbent pad. The inner side of the absorbent pad is formed with the groove 26 extending from the distal end of the cutout 21 toward the lower end 6B of the absorbent pad. Of upper and lower portions of the absorbent pad partially divided by the cutout 21, any one portion is formed on the backsheet 2 with the fastening zone 24.

While the absorbent pad is preferably of rectangular shape defined by the longitudinally opposite ends 6A, 6B extending in parallel to each other and the transversely opposite side edges 7A, 7B also extending in parallel to each other, it is also possible to configure the transversely opposite side edges 7A, 7B so that the folded absorbent pad may present a trapezoidal shape. An arrangement is also possible in which at least one of the longitudinally opposite ends 6A, 6B is curved so that these ends 6A, 6B are substantially in parallel to each other. As the topsheet 1 in this variant of the absorbent pad, liquid-permeable nonwoven fabric or porous plastic film may be employed. As the backsheet 2, liquid-impermeable or air-impermeable plastic film or nonwoven fabric or plastic film having its outer surface adhesively covered with nonwoven fabric may be employed. Topsheet 1 and backsheet 2 may be bonded together by means of adhesive agent such as hot melt adhesive and, if at least one of these sheets 1, 2 contains heat-sealable plastic material, these sheets 1, 2 may be bonded together by heat-sealing effect of such plastic material. The absorbent core 3 may be made of fluff pulp or a mixture of fluff pulp and polymer particles of high water absorptivity. As the flap 31, liquid-permeable or liquid-impermeable nonwoven fabric or plastic film may be employed.

The urine absorbent pad according to the invention can be easily worn since the absorbent pad is adapted to be folded to form a bag wrapping a wearer's penis after the penis has been inserted into the through-hole of the absorbent pad in its unfolded state and there is no apprehension that the penis might easily fall off from the absorbent pad after the pad has been worn since the penis can be reliably inserted into the through-hole deeply to its proximal end.

According to the invention, insertion of the wearer's penis into the pad is further facilitated by utilizing the U-shaped cutout as the means for insertion of the wearer's penis rather than the simple through-hole.

In this embodiment adopting the U-shaped cutout, the backsheet of the absorbent pad may be formed with the fastening zone to wrap the penis with the portion of the absorbent pad defining the U-shaped cutout and thereby prevent the absorbent pad from falling off the penis.

By forming the one of longitudinally opposite ends of the absorbent pad with the second adhesive zone, it is assured that the pad worn by the patient is sealed along its all sides and thereby urine leakage preventing function of the absorbent pad can be improved.

Preferably the flaps are affixed to the inner side of the absorbent pad so that the one side edge of each such flap may be elastically biased to rise on the topsheet and thereby to form the pocket serving to prevent urine from leaking aside from the absorbent pad.

Preferably the inner side of the absorbent pad is formed with the groove by which the wearer's penis can be properly positioned and oriented.

What is claimed is:

1. A urine absorbent pads comprising a liquid-permeable topsheet; a liquid-impermeable backsheet and a liquid-absorbent core disposed therebetween, wherein:

the absorbent pad is foldable with the topsheet defining a folding line extending across a full width of the absorbent pad at a desired level to divide the absorbent pad into longitudinally upper and lower halves when the topsheet is folded onto itself along the folding line, wherein the topsheet is formed on an inner surface thereof with transversely opposite adhesive zones each extending over a predetermined extent of each of side edges of the topsheet including the folding line, and wherein one of the upper and lower halves divided by the folding line is formed with a guide arrangement extending through the topsheet, backsheet and core from an inner surface to an outer surface of the absorbent pad for insertion of a wearer's penis, said transversely opposite adhesive zones being operable to be adhesively secured to opposing regions of the topsheet after the wearer's penis is inserted through the guide arrangement in the unfolded state of the pad so as to securely retain the pad to its folded state on the penis.

2. The urine absorbent pad according to claim 1, wherein the guide means for insertion of the wearer's penis comprises a substantially U-shaped cutout extending from a middle of one end toward the other end of the absorbent pad so as to divide a portion of the absorbent pad in transversely two halves.

3. The urine absorbent pad according to claim 2, wherein the backsheet of the absorbent pad is formed on one of the transversely two halves divided by the U-shaped cutout with a fastening zone to which the other of the transversely two halves can be detachably fastened.

4. The urine absorbent pad according to claim 1, wherein a transversely middle region of the absorbent pad in a folded state thereof which includes the guide arrangement is thinner than a surrounding region of the absorbent pad as a result of the topsheet being recessed toward the backsheet in the transversely middle region so as to form a groove extending longitudinally of the absorbent pad in the folded state thereof.

5. The urine absorbent pad according to claim 1, wherein the guide arrangement for insertion of the wearer's penis comprises a cutout substantially of U-shape that extends from one of the side edges of the topsheet toward the other side edge and terminating at a transversely middle region of the absorbent pad in its folded state so as to divide a portion of the absorbent pad limited by the cutout into upper and lower regions.

6. A urine absorbent pad, comprising a liquid-permeable topsheet; a liquid-impermeable backsheet and a liquid-absorbent core disposed therebetween, wherein:

the absorbent pad is foldable with the topsheet defining a folding line extending across a full width of the absorbent pad at a desired level to divide the absorbent pad into longitudinally upper and lower halves when the topsheet is folded onto itself along the folding line, wherein the topsheet is formed on an inner surface thereof with transversely opposite adhesive zones each extending over a predetermined extent of each of side edges of the topsheet including the folding line, and wherein one of the upper and lower halves divided by the folding line is formed with a guide arrangement extending through the topsheet, backsheet and core from an inner surface to an outer surface of the absorbent pad for insertion of a wearer's penis, wherein the guide arrangement for insertion of the wearer's penis comprises a circular through-hole formed in a transversely middle region of the absorbent pad in the folded state thereof.

7. The urine absorbent pad according to claim 6, said transversely opposite adhesive zones being operable to be adhesively secured to opposing regions of the topsheet after the wearer's penis is inserted through the guide arrangement in the unfolded state of the pad so as to securely retain the pad to its folded state on the penis.

8. A urine absorbent pad, comprising a liquid-permeable topsheet; a liquid-impermeable backsheet and a liquid-absorbent core disposed therebetween, wherein:

the absorbent pad is foldable with the topsheet defining a folding line extending across a full width of the absorbent pad at a desired level to divide the absorbent pad into longitudinally upper and lower halves when the topsheet is folded onto itself along the folding line, wherein the topsheet is formed on an inner surface thereof with transversely opposite adhesive zones each extending over a predetermined extent of each of side edges of the topsheet including the folding line, and wherein one of the upper and lower halves divided by the folding line is formed with a guide arrangement extending through the topsheet, backsheet and core from an inner surface to an outer surface of the absorbent pad for insertion of a wearer's penis, wherein at least one of longitudinally opposite ends of the topsheet is formed on an inner surface thereof with a second adhesive zone.

9. The urine absorbent pad according to claim 8, wherein the said adhesive zones are continuous with the second adhesive zone.

10. The urine absorbent pad according to claim 8, said transversely opposite adhesive zones being operable to be adhesively secured to opposing regions of the topsheet after the wearer's penis is inserted through the guide arrangement in the unfolded state of the pad so as to securely retain the pad to its folded state on the penis.

11. A urine absorbent pad, comprising a liquid-permeable topsheet; a liquid-impermeable backsheet and a liquid-absorbent core disposed therebetween, wherein:

the absorbent pad is foldable with the topsheet defining a folding line extending across a full width of the absorbent pad at a desired level to divide the absorbent pad into longitudinally upper and lower halves when the topsheet is folded onto itself along the folding line, wherein the topsheet is formed on an inner surface thereof with transversely opposite adhesive zones each extending over a predetermined extent of each of side edges of the topsheet including the folding line, and wherein one of the upper and lower halves divided by the folding line is formed with a guide arrangement extending through the topsheet, backsheet and core from an inner surface to an outer surface of the absorbent pad for insertion of a wearer's penis, further comprising a pair of flaps each defined by a pair of transversely opposite side edges extending substantially in parallel to each other and a pair of longitudinally opposite ends extending also substantially in parallel to each, said flaps being located inside the transversely opposite adhesive zones and each flap being bonded to the inner surface of the topsheet along one of the side edges of each flap and both ends thereof, each flap having an elastic member bonded under appropriate tension to the flap along the other of the side edges so that the elastic member contracts as the absorbent pad is folded along the folding line, whereby the flap tends to stand erect on the inner surface of the topsheet with the one side edge remaining on the inner surface of the absorbent pad as a proximal edge of the flap while the other side edge is lifted off from the inner surface of the topsheet.

12. The urine absorbent pad according to claim 11, said transversely opposite adhesive zones being operable to be adhesively secured to opposing regions of the topsheet after the wearer's penis is inserted through the guide arrangement in the unfolded state of the pad so as to securely retain the pad to its folded state on the penis.

13. A urine absorbent pad, comprising a liquid-permeable topsheet; a liquid-impermeable backsheet and a liquid-absorbent core disposed therebetween, wherein:

the absorbent pad is foldable with the topsheet defining a folding line extending across a full width of the absorbent pad at a desired level to divide the absorbent pad into longitudinally upper and lower halves when the topsheet is folded onto itself along the folding line, wherein the topsheet is formed on an inner surface thereof with transversely opposite adhesive zones each extending over a predetermined extent of each of side edges of the topsheet including the folding line, and wherein one of the upper and lower halves divided by the folding line is formed with a guide arrangement extending through the topsheet, backsheet and core from an inner surface to an outer surface of the absorbent pad for insertion of a wearer's penis wherein the guide arrangement for insertion of the wearer's penis comprises a cutout substantially of U-shape that extends from one of the side edges of the topsheet toward the other side edge and terminating at a transversely middle region of the absorbent pad in its folded state so as to divide a portion of the absorbent pad limited by the cutout into upper and lower regions, wherein a fastening zone is disposed on a rear side of the absorbent pad on one of the upper and lower regions divided by the cutout to which fastening zone the other of the upper and lower regions is detachably fastened to secure the upper and lower regions to each other around the wearer's penis.

14. The urine absorbent pad according to claim 13, said transversely opposite adhesive zones being operable to be adhesively secured to opposing regions of the topsheet after the wearer's penis is inserted through the guide arrangement in the unfolded state of the pad so as to securely retain the pad to its folded state on the penis.

15. A urine absorbent pad, comprising a liquid-permeable topsheet; a liquid-impermeable backsheet and a liquid-absorbent core disposed therebetween, wherein:

the absorbent pad is foldable with the topsheet defining a folding line extending across a full width of the absorbent pad at a desired level to divide the absorbent pad into longitudinally upper and lower halves when the topsheet is folded onto itself along the folding line, wherein the topsheet is formed on an inner surface thereof with transversely opposite adhesive zones each extending over a predetermined extent of each of side edges of the topsheet including the folding line, and wherein one of the upper and lower halves divided by the folding line is formed with a guide arrangement extending through the topsheet, backsheet and core from an inner surface to an outer surface of the absorbent pad for insertion of a wearer's penis, wherein the guide arrangement for insertion of the wearer's penis comprises a cutout substantially of U-shape that extends from one of the side edges of the topsheet toward the other side edge and terminating at a transversely middle region of the absorbent pad in its folded state so as to divide a portion of the absorbent pad limited by the cutout into upper and lower regions, wherein a transversely middle region of the absorbent pad in its folded state is thinner than a surrounding region of the absorbent pad and the topsheet is recessed toward the backsheet in the transversely middle region so as to form a longitudinally extending groove which intersects the transversely extending cutout for insertion of the wearer's penis.

* * * * *